United States Patent [19]

Celmer et al.

[11] 4,431,801
[45] Feb. 14, 1984

[54] POLYCYCLIC ETHER ANTIBIOTIC

[75] Inventors: Walter D. Celmer, New London; Walter P. Cullen, East Lyme, both of Conn.; Riichiro Shibakawa, Handa; Junsuke Tone, Chita, both of Japan

[73] Assignee: Pfizer Inc., New York, N.Y.

[21] Appl. No.: 401,234

[22] Filed: Jul. 23, 1982

Related U.S. Application Data

[62] Division of Ser. No. 285,264, Jul. 20, 1981, Pat. No. 4,361,649.

[51] Int. Cl.$^3$ ............................................... C07H 3/06
[52] U.S. Cl. ..................................... 536/123; 536/1.1; 536/18.1
[58] Field of Search ...................... 536/1.1, 18.1, 123

[56] References Cited

U.S. PATENT DOCUMENTS

| | | | |
|---|---|---|---|
| 2,771,392 | 11/1956 | Tanner et al. | 536/7.1 |
| 2,991,230 | 7/1961 | Kita | 435/57 |
| 4,022,885 | 5/1977 | Celmer et al. | 424/122 |
| 4,269,971 | 5/1981 | Yamagishi et al. | 536/123 |
| 4,283,493 | 8/1981 | Liu et al. | 435/119 |
| 4,293,650 | 10/1981 | Florent et al. | 435/119 |
| 4,366,311 | 12/1982 | Mizutani et al. | 536/123 |

OTHER PUBLICATIONS

Agtarap et al., J. Amer. Chem. Soc., 89, 5737 (1967).
Steinrauf et al., Biochem. Biophys. Res. Communs., 33, 29 (1968).
Gachon et al., J. Chem. Soc., Chem. Communs., 1421 (1970).
Hamill et al., J. Antibiotics, 22, 161 (1969).
Miyazaki et al., J. Antibiotics, 27, 814 (1974).
Bissell et al., J. Chem. Soc., Chem. Communs., 967 (1972).
Blount et al., J. Chem. Soc., Chem. Communs., 927 (1971).
Jones et al., J. Amer. Chem. Soc., 95, 3399 (1973).
Fehr et al., J. Antibiotics, 30, 903 (1977).
Toeplitz et al., J. Amer. Chem. Soc., 101, 3344 (1979).
Tsuji et al., J. Antibiotics, 32, 169 (1979).
Tsuji et al., J. Antibiotics, 33, 94 (1980).
Mizutani et al., J. Antibiotics 33, 137 (1980).
Dorman et al., J. Antibiotics 33, 252 (1980).
Westley, Adv. Appl. Microbiol., 22, 177–222 (1977).

Primary Examiner—Dolph H. Torrence
Assistant Examiner—Ciro Joseph Faroci
Attorney, Agent, or Firm—Connolly and Hutz

[57] ABSTRACT

An antibiotic having the formula

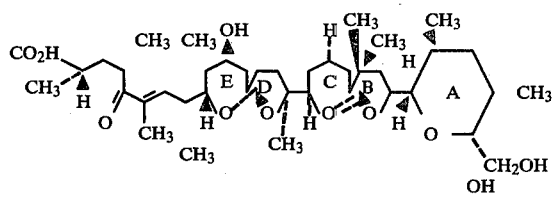

and the pharmaceutically acceptable salts thereof.

3 Claims, 2 Drawing Figures

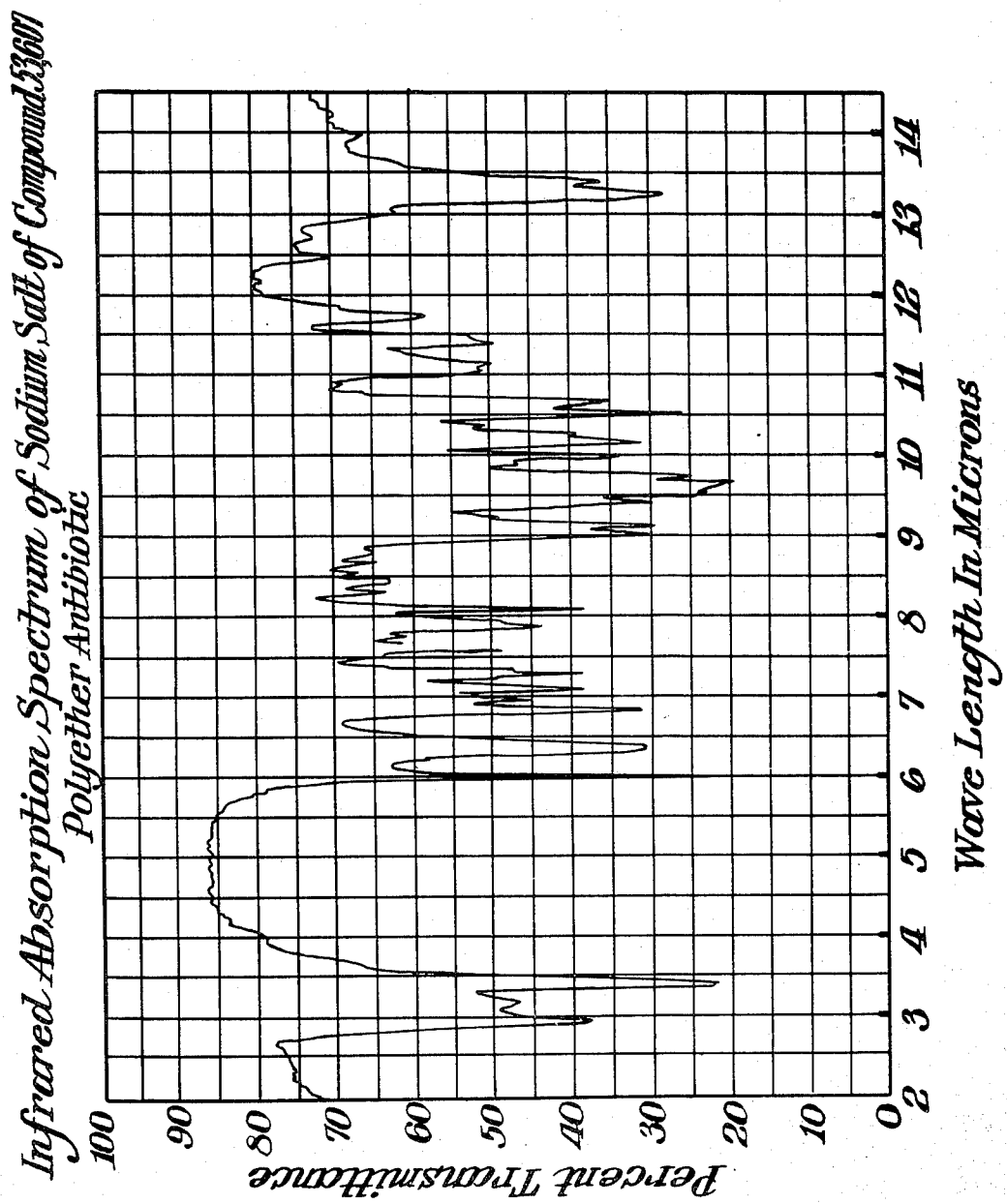

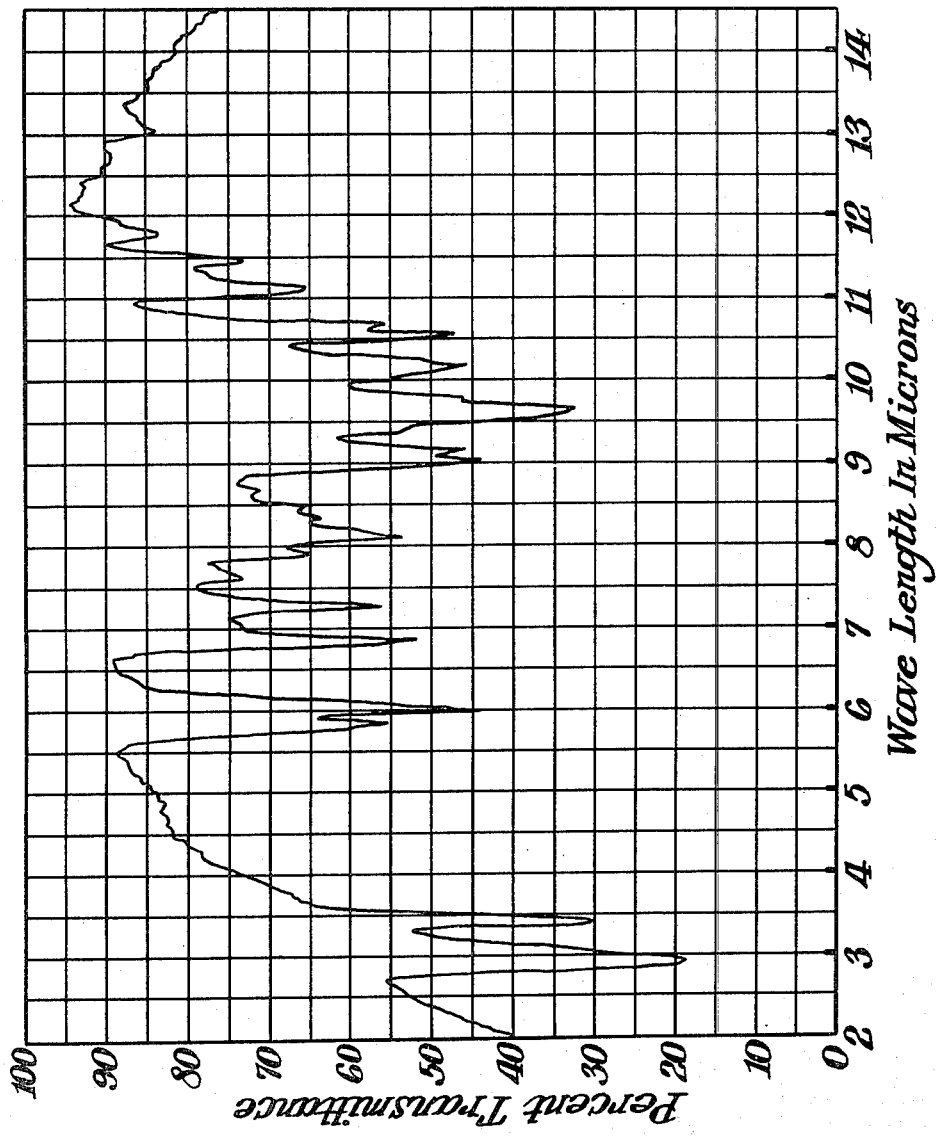

POLYCYCLIC ETHER ANTIBIOTIC

CROSS REFERENCE TO RELATED APPLICATION

This is a division of application Ser. No. 285,264 filed July 20, 1981, U.S. Pat. No. 4,361,649.

BACKGROUND OF THE INVENTION

This invention is concerned with a new member of the acidic polycyclic ether group of antibiotics, a class of compounds characterized biologically by their effect on cation transport in mitochondria. This family of antibiotics includes monensin [*J. Amer. Chem. Soc.*, 89-5737, (1967)]; nigericin [*Biochem. Biophys. Res. Comm.*, 33:29, (1968)]; grisorixin [*J. Chem.Soc.,Chem. Commun.*, 1421, (1970)]; dianemycin [*J. Antibiotics* 22:161, (1969)]; salinomycin [*J. Antibiotics*, 27:814, (1974)]; X-537A [*J.Chem.Soc., Chem. Commun.*, 967, (1972)]; X-206 [*J.Chem.Soc.Chem.Commun.*, 927, (1971)]; A204A [*J.Amer.Chem.Soc.*, 95:3399,(1973)]; mutalomycin [*J. Antibiotics*, 30:903, (1977)]; ionomycin [*J. Amer.Chem.Soc.*, 101:3344, (1979)]; K-41B [*J. Antibiotics*, 32:169, (1979)]; A-130B and A-130C [*J. Antibiotics*, 33:94, (1980)]; leuseramycin [*J. Antibiotics*, 33:137, (1980)]; and A-28695 B [*J. Antibiotics*, 33:252, (1980)]. Also, the subject has been reviewed by Westley, "Polyether Antibiotics," Adv. Appl. Microbiol., 22:177 (1977).

The polycyclic ether antibiotics listed above are active against Gram-positive bacteria, fungi and protozoa. These antibiotics exhibit potent anticoccidial activity.

The well-known protozoan disease, coccidiosis, continues to be a serious problem and its control is of economic importance to veterinary science, especially to the poultry industry. Coccidiosis results from infection by one or more species of Eimeria or Isospora (for a summary, see Lund and Farr in "Disease of Poultry," 5th ed, Biester and Schwarte, Eds., Iowa State University Press, Ames, Ia., 1965, pp. 1056-1096). There are six species of coccidia which produce easily discernible morbidity in susceptible chickens. *Eimeria tenella, E. necatrix. E. brunetti. E. acervulina, E. maxima* and *E. mivati* produce damage either directly through destruction of epithelial cells of the digestive tract or indirectly through production of toxins. Three other species of protozoa belonging to the same genus are considered to be relatively innocuous; however, *E. mitis, E. hagani* and *E. praecox* are capable of reducing weight gain, lowering feed efficiency and adversely affecting egg production.

In view of the greater economic losses due to coccidiosis and the disadvantages of some known anticoccidial agents, the search for better anticoccidial agents continues.

Enteritis is another disease which can cause severe economic losses to livestock producers. Enteritis occurs in chickens, swine, cattle and sheep and is attributed mainly to anaerobic bacteria, particularly *Clostridium perfringens*, and viruses. Enterotoxemia in ruminants, an example of which is "overeating disease" in sheep, is a condition caused by *C. perfringens* infection.

Swine dysentery is one of the most common swine diseases diagnosed in the United States. Additionally, the disease is prevalent in many other countries and annually causes many thousands of dollars losses in stock to swine growers around the world. It has recently been discovered that a large spirochete is the causative organism of the disease. This organism, *Treponema hyodysenteriae*, has now been isolated and shown to be capable of producing the disease [Harris, D. L. et al.: "Swine Dysentery-1 Inoculation of Pigs with Treponema hyodysenteriae (New Species) and Reproduction of the Disease," *Vet. Med/SAC,*67: 61-64: 1972]. The test data recited hereinafter concerns tests conducted with this organism. It must be noted that it is not known whether *T. hyodysenteriae* is the sole causative organism of swine dysentery. From the data available, however, it can be concluded that it is a primary source of the infection.

Performance enhancement (increased rate of growth and/or increased efficiency of feed utilization) in ruminants, such as cattle, is another economically desirable objective of veterinary science. Of particular interest is growth promotion achieved by increasing feed-utilization efficiency. The mechanism for utilization of the major nutritive portion (carbohydrates) of ruminant feeds is well known. Microorganisms in the rumen of the animal degrade carbohydrates to produce monosaccharides and then convert these monosaccharides to pyruvate compounds. Pyruvates are metabolized by microbiological processes to form acetates, butyrates or propionates, collectively known as volatile fatty acids (VFA). For a more detailed discussion, see Leng in "Physiology of Digestion and Metabolism in the Ruminant," Phillipson et al., Eds., Oriel Press, Newcastle-upon-Tyne, England, 1970, pp 408-410.

The relative efficiency of VFA utilization is discussed by McCullough in "Feedstuffs," June 19, 1971, page 19; Eskeland et al. in J. An. Sci. 33, 282 (1971); and Church et al. in "Digestive Physiology and Nutrition of Ruminants," Vol. 2 1971, pp. 622 and 625. Although acetates and butyrates are utilized, propionates are utilized with greater efficiency. Furthermore, when too little propionate is available, animals may develop ketosis. A beneficial compound, therefore, stimulates animals to produce a higher proportion of propionates from carbohydrates, thereby increasing carbohydrate utilization efficiency and also reducing the incidence of ketosis.

Yet another disease which causes economic losses to livestock producers is caused by the protozoan parasite of the genus Theileria. That disease, theileriosis, is also known as "East Coast Fever," "Coaster fever" or "Rhodesian tick fever." The Theileria parasite invades but does not destroy red blood cells which gives rise to acute or chronic febrile infections. In cattle the disease is characterized by high fever, swelling of the lymph nodes, emaciation and high mortality. The disease is a very serious problem in East and Central Africa. For a more detailed discussion of theileriosis, see "The Merck Veterinary Manual," Siegmund et al., Eds., Merck & Co., Rahway, N.J., 5th Ed., pp. 431-433 (1979).

SUMMARY OF THE INVENTION

This invention is concerned with a new acidic polycyclic ether antibiotic produced by the submerged aerobic propagation in aqueous nutrient media of *Streptomyces halstedii* ATCC 31812 isolated from a soil sample from Japan. The antibiotic and its cationic salts are active against a variety of microorganisms and are effective in controlling coccidiosis, enteritis, swine dysentery and theileriosis as well as being effective in promotion of growth in poultry and ruminants.

DESCRIPTION OF THE DRAWINGS

The following infrared absorption spectra in potassium bromide are presented in the drawings:

FIG. 1—Antibiotic 53,607 in the sodium salt form;
FIG. 2—Antibiotic 53,607 in the free acid form.

DETAILED DESCRIPTION OF THE INVENTION

The antibiotic producing microorganism of the present invention was isolated from a soil sample collected in Hiroshima, Japan. The microorganism was found on examination to have the morphological features of a Streptomyces. It was found to have narrow hyphae of the Actinomycetales and aerial mycelium with chains of spores characteristic of the genus Streptomyces. The generic identity was further supported by cell wall analysis.

A culture of the microorganism was inoculated from a slant into liquid ATCC #172 medium and grown for 4 days at 28° C. on a shaker. It was then removed from the shaker, centrifuged, washed three times with sterile distilled water and planted on media commonly used for identification of members of the Actinomycetales.

Incubation was at 28° C. except where noted otherwise, and results were recorded at appropriate times; results given here are after 2 weeks of incubation except where otherwise noted.

Identification media used for the characterization of the culture and references for their composition are as follows:

1. Tryptone Yeast Extract Broth—(ISP #1 medium, Difco).
2. Yeast Extract-Malt Extract Agar—(ISP #2 medium, Difco).
3. Oatmeal Agar—(ISP #3 medium, Difco).
4. Inorganic Salts-Starch Agar—(ISP #4 medium, Difco).
5. Glycerol-Asparagine Agar—(ISP #5 medium, Difco).
6. Peptone-Yeast Extract Iron Agar—(ISP #6 medium, Difco).
7. Czapek-Sucrose Agar—S. A. Waksman, "The Actinomycetes," Vol. 2, medium no. 1, p. 328, 1961.
8. Glucose-Asparagine Agar—Ibid, medium no. 2, p. 328.
9. Bennett's Agar—Ibid, medium no. 30, p. 331.
10. Emerson's Agar—Ibid, medium no. 28, p. 331.
11. Nutrient Agar—Ibid, medium no. 14, p. 330.
12. Gordon and Smith's Tyrosine Agar—R. E. Gordon and M. M. Smith, Jr. Bact. 69: 147–150, 1955.
13. Casein Agar—Ibid.
14. Calcium Malate Agar—S. A. Waksman, Bact. Rev. 21: 1–29, 1957.
15. Gelatin—R. E. Gordon and J. M. Mihm, Jr. Bact. 73: 15–27, 1957.
16. Starch—Ibid.
17. Organic Nitrate Broth—Ibid.
18. Dextrose Nitrate Broth—S. A. Waksman, The Actinomycetes, Vol. 2, medium no. 1, p. 328, 1961, with 3 g dextrose substituted for 30 g sucrose and agar omitted.
19. Potato Carrot Agar—M. P. Lechevalier, Jr. Lab. and Clin, Med. 71: 934–944, 1968 but use only 30 g potatoes, 2.5 g carrots and 20 g agar.
20. 2% Tap Water Agar.
21. Skim Milk—Difco.
22. Cellulose utilization
    (a) H. L. Jensen, Proc. Linn. Soc. N.S.W. 55: 231–248, 1930.
    (b) M. Levine and H. W. Schoenlein, "A Compilation of Culture Media," medium no. 2511, 1930.
23. Carbohydrates—ISP #9 medium, Difco; Nonomura and Ohara's C-2 medium in Nonomura, H. and Y. Ohara, J. Ferment. Technol. 49: 887–894, 1971.
24. Temperature Range—ATCC medium 172 in "ATCC Culture Collection Catalogue," 14th ed., p. 518, 1980.

The new culture (Pfizer N393-39) was described as follows on the various media with colors described in common terminology, but exact colors were determined by comparison with color chips from the *Color Harmony Manual*, fourth edition:

Yeast Extract-Malt Extract Agar
Growth good, cream to pale yellowish (near 2 ca), moderately raised, smooth, roughened to wrinkled, no aerial mycelium; reverse same as surface; no soluble pigment.

Oatmeal Agar
Growth moderate, grey to brownish grey (2 ge, 2 lg to 2 ni), thin to slightly raised, smooth with small white dots; aerial mycelium sparse, white to pale greyish; reverse same as surface; soluble pigment pale yellowish.

Inorganic Salts-Starch Agar
Growth moderate, yellowish brown to brown (2 ic, 3 ne to 3 le), thin, smooth, no aerial mycelium; reverse same as surface; no soluble pigment.

Glycerol-Asparagine Agar
Growth poor to moderate, dull white, thin, smooth with a few small white dots; aerial mycelium sparse, white; reverse same as surface; no soluble pigment.

Gordon and Smith's Tyrosine Agar
Growth poor to moderate, colorless to cream (2 ca), thin smooth, no aerial mycelium; reverse same as surface; no soluble pigment.

Czapek-Sucrose Agar
Growth poor, colorless to dull white, thin, smooth, with a few small white dots of aerial mycelium; reverse same as surface; no soluble pigment.

Glucose-Asparagine Agar
Growth moderate, yellowish grey to lavender grey (2 ig, 3 ge to 3 ig), thin, smooth but slightly wrinkled near the edge; aerial mycelium pale greyish (2ge); reverse same as surface; soluble pigment pale yellowish.

Calcium Malate Agar
Growth poor, colorless with a dull white margin, submerged, smooth, with small dots of greyish (near gray series 2 dc to 2 fe) aerial mycelium; reverse same as surface; no soluble pigment.

Casein Agar
Growth moderate, pale brownish (2 ne to 3 ne), thin, smooth to slightly roughened, no aerial mycelium; reverse same as surface; no soluble pigment.

Bennett's Agar
Growth good, brown (3 ng to 3 ni), raised, wrinkled, no aerial mycelium; reverse same as surface; soluble pigment pale yellowish (2 ca).

Emerson's Agar
Growth moderate to good, pale yellowish brown (2 ca to 3 ca) to greenish grey (23 ge to 23 ig), thin to raised, smooth to slightly roughened or occurring as membraneous cups which were irregularly wrinkled, no aerial mycelium; reverse same as surface; no soluble pigment.

Nutrient Agar

Growth poor to moderate, pale yellowish (2 ca), thin, smooth, no aerial mycelium; reverse same as surface; no soluble pigment.

Gelatin Agar

Growth moderate, pale yellowish (2 ca), thin, smooth, no aerial mycelium; reverse same as surface; no soluble pigment.

Starch Agar

Growth good, cream, pale yellowish to pale yellowish brown (2 ca to near 3 gc), thin to slightly raised, smooth but wrinkled toward the edge, no aerial mycelium; reverse same as surface; no soluble pigment.

Potato Carrot Agar

Growth moderate, cream (2 ca) with a greyish to dark greyish margin (near gray series 2 fe, 2 ih to 2 ml), thin, smooth aerial mycelium grey to dark grey; reverse same as surface; no soluble pigment.

Tap Water Agar

Growth poor, colorless to dull white, thin, smooth, with a few small white dots of aerial mycelium; reverse same as surface; no soluble pigment.

The biochemical properties notes are summarized as follows:

1. Melanin not produced
2. Hydrogen sulfide not produced
3. Gelatin liquefied
4. Starch hydrolyzed
5. Nitrate reduced to nitrite
6. Scant growth on Jensen's cellulose
7. No growth on Levine and Schoenlein's cellulose
8. No decomposition on both cellulose media
9. No coagulation on milk
10. No peptonization on milk
11. No digestion of casein, calcium malate and tyrosine
12. Carbohydrate Utilization:
    I. On Nonomura's medium, glucose, arabinose and xylose utilized; raffinose doubtfully utilized; sucrose, inositol, mannitol, fructose and rhamnose not utilized.
    II. On ISP #9 medium, glucose, arabinose, xylose and sucrose utilized; fructose, inositol, mannitol, raffinose, and rhamnose not utilized.

The following morphological observations were made on potato carrot agar after 15 days of incubation:

Spore mass in gray color series; spore chains straight, curved, irregularly flexuous or wavy, rarely hooked, 10 to 30 spores per spore chain, rarely less than 10 spores per spore chain; spores oval, elliptical to rod-shaped, $1-1.8 \times 0.8-0.9$ μm., smooth, as revealed by scanning electron microscopy.

The relationship of temperature to growth rate was observed as follows:

| Temperature | Growth |
|---|---|
| 21° C. | Good to Excellent |
| 28° C. | Good |
| 37° C. | Moderate |
| 45° C. | Poor |

As noted above, cell wall analysis supported the generic identity of the culture as a species of Streptomyces. Whole-cell analysis revealed the presence of LL-diaminopimelic acid and glycine but the absence of diagnostic sugars. The methods used for whole-cell amino acid and sugar analyses are described in Becker, B. et al, *Appl. Microbiol.*, 12: 421–423, 1964; and in Lechevalier, M. P., *J. Lab. Clin. Med.*, 71: 934–944, 1968.

Culture N393-39 is characterized by pale gray to gray color of spores in mass, straight to flexuous spore chains, smooth spores and inability to produce melanin. The presence of LL-diaminopimelic acid and the absence of diagnostic sugars in the whole-cell hydrolysates establish the assignment of it to the genus Streptomyces. The culture closely resembles *Streptomyces halstedii* described in Shirling, E. B. and Gottlieb, D., 1968, Int. J. Syst. Bacteriol., 18:69–189, and thus the type strain of *S. halstedii* ATCC 10897 was used for comparison. Both cultures agree with each other in the following properties: morphology of spore chains, morphology of spore surface, negative melanin production, and more of the biochemical properties. Culture N393-39 differs from *S. halstedii* in the absence of aerial mycelium on many media; brownish rather than grayish to black colony reverse on ISP#2, ISP#3, and ISP#4 media; negative $H_2S$ production and inability to utilize fructose. Since these differences are merely minor variations among strains of a Streptomyces species, N393-39 is considered as a new strain of *Streptomyces halstedii* (Waksman and Curtis) Waksman and Henrici.

The new culture (Pfizer N393-39) was submitted on Feb. 23, 1981, to the American Type Culture Collection, Rockville, Maryland and given the designation *Streptomyces halstedii* ATCC 31812. The permanency of the deposit of this culture at The American Type Culture Collection at Rockville, Maryland and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

Cultivation of the culture *Streptomyces halstedii* ATCC 31812 may be conducted under conditions similar to those employed in previous fermentations yielding polyether antibiotics. See, for example, U.S. Pat. No. 4,195,079. Cultivation preferably takes place in aqueous nutrient media under submerged aerobic conditions with agitation at a temperature of 24° to 36° C. Nutrient media useful for cultivation include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, magnesium, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of sterile free air per volume of fermentation broth per minute forced into the broth through a sparger. Agitation may be maintained by means of agitators generally familiar to those skilled in the fermentation art. The rate of agitation depends on the type of agitator employed. A shake flask is usually run at 150 to 200 cycles per minute whereas a fermentor is usually run at 300 to 600 revolutions per minute. Aseptic conditions must, of course, be maintained through the transfer of the organism and throughout its growth.

Inoculum for the preparation of the antibiotic according to this invention may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum in submerged inoculum tanks will usually be at the most favorable period in 1½ to 3 days.

The progress of antibiotic production during fermentation and the bioactivity of the fermentation broth can be monitored by biological assay of the broth employing a sensitive strain of *Straphylococcus aureus* or *Bacillus subtilis*. *S. aureus* ATCC 6538 and *B. subtilis* ATCC 6633 are suitable strains for this purpose. Standard plate assay technique is employed in which the zone of inhibition surrounding a filter paper disc saturated with the broth is used as a measure of antibiotic potency. Also, thin-layer chromatography employing silica gel is a useful tool for analyzing the antibiotic produced in fermentation media and the composition of crude and purified materials extracted from the fermentation broths. The Analtech silica gel GF chromatograms are developed with ethyl acetate/methanol (9:1) or chloroform/methanol (9:1). The antibiotic compound is visualized by spraying with vanillin in ethanolic sulfuric acid (3 g. vanillin in 97 ml. ethanol and 3 ml. concentrated sulfuric acid) and heating the TLC plate at 80° C. The antibiotic appears as a pinkish spot. The plate can also be overlayed with agar seeded with either *S. aureus* or *B. subtilis* and incubated at 37° C. for 16 hours to visualize the antibiotic.

The antibiotic produced by fermentation of *S. halstedii* ATCC 31812 may be separated and recovered by extracting the whole, unfiltered fermentation broth with an organic solvent such as chloroform, ethyl acetate, methylisobutyl ketone or butanol at the naturally prevailing pH. The solvent extract can then be concentrated *in vacuo* to a thin syrup.

A typical method of separation and recovery of the antibiotic of this invention (hereafter "Antibiotic Compound 53,607") is as follows:

The whole broth from fermentation of *S. halstedii* ATCC 31812 was extracted with methylisobutyl ketone. The solvent extract yielded a dark oil on solvent evaporation under vacuum. The oil was dissolved in chloroform and poured onto a bed of silica gel. The silica gel bed was then washed successively with chloroform, ethyl acetate and acetone. The wash fractions were examined by thin-layer chromatography and Antibiotic Compound 53,607 was found almost exclusively in the ethyl acetate fraction. The ethyl acetate fraction was evaporated to dryness and the other fractions ere discarded. The dry ethyl acetate fraction was further purified by column chromatography by being taken up in ethyl acetate and added to a column packed with silica gel slurried in ethyl acetate and eluted with ethyl acetate. Column cuts containing Antibiotic Compound 53,607 (determined by thin-layer chromatography) were combined and the volume reduced by evaporation. This material was then chromatographed on a column packed with Sephadex LH-20 in methanol and the fractions containing Antibiotic Compound 53,607 were combined, evaporated to a reduced volume and then taken up in chloroform. The chloroform solution was washed with 5% monosodium phosphate buffer adjusted to pH 4.5 with phosphoric acid. The solvent phase is then washed with 5% w/v disodium phosphate buffer the pH of which was adjusted to 9.0 with sodium hydroxide solution. The solvent phase is then dried over anhydrous sodium sulfate and evaporated. The residue was taken up in acetone and placed in a refrigerator whereupon Antibiotic Compound 53,607 crystallized as the sodium salt. The free acid can be obtained by washing an ethyl acetate solution of the sodium salt with water adjusted to pH 4.5. Evaporation of the solvent afforded crystals of the free acid of Antibiotic Compound 53,607.

Analysis of Antibiotic Compound 53,607 indicates the following structure

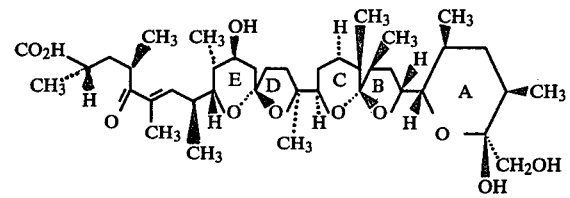

Antibiotic Compound 53,607 exhibits inhibitory action against the growth of a number of Gram-positive microorganisms. In Table I, below, the results of *in vitro* MIC tests are summarized. For this test each organism is inoculated in a series of test tubes containing nutrient medium and varying concentrations of Compound 53,607 to determine the minimal concentration of the antibiotic in mcg/ml which inhibits the growth of the organism over a period of 24 hours (MIC).

TABLE I

| Organism | | MIC, mcg./ml Compound 53,607 (sodium salt) |
|---|---|---|
| Staphylococcus aureus | 01A005 | 0.78 |
| | 01A052 | 0.78 |
| | 01A110 | 1.56 |
| | 01A400 | 1.56 |
| Streptococcus faecalis | 02A006 | 1.56 |
| Streptococcus pyogenes | 020203 | <0.01 |
| Corynebacterium pyogenes | 11D001 | 25 |
| Bacillus subtilis | 06A001 | 0.39 |
| Bacteroides fragilis | 78C004 | 12.5 |
| | 78C009 | 6.25 |
| | 78C010 | 6.25 |
| Bacteroides vulgatis | 78E032 | 3.12 |
| Haemophilus influenza | 54A036 | 6.25 |
| | 54A037 | 3.12 |
| | 54A059 | 12.5 |
| Pasteurella multocida | 59A001 | >200 |
| Clostridium perfringens | 10A002 | 0.98 |
| | 10A003 | 0.98 |
| Neisseria sicca | 66C000 | 25 |
| Staphylococcus epidermidis | 01B087R | 0.78 |
| | 01B111RR | 0.78 |
| | 01B126 | 1.56 |
| Fusobacterium necrophorum | 84C004 | 3.12 |
| Treponema hyodysenteriae | 94A001 | 0.39 |
| | 94A002 | 0.098 |

Against the gram-negative bacteria such as *Escherischia coli, Pseudomonas aeruginosa, Klebsiella pneumoniae, Serratia marcescens* and *Enterobacteriacese aerogenes,* MIC values were >50 in each case.

Antibiotic Compound 53,607 and its cationic salts exhibit excellent activity against coccidial infections in poultry. When incorporated into the diet of chickens at levels of 50 to 200 ppm, these compounds are effective in controlling infections due to *Eimeria tenella, E. acervulina, E. maxima, E. brunetti* and *E. necatrix*.

Efficacy data for Antibiotic Compound 53,607 and its salts against coccidial infections in chickens was obtained in the following fashion. Groups of 3-5 ten-day old SPF white leghorn cockerel chicks were fed a mash diet containing Antibiotic Compound 53,607 or its sodium and/or potassium salt uniformly dispersed therein. After being on this ration for 24 hours each chick was inoculated *per os* with oocysts of the particular species of Eimeria being tested. Other groups of 3-5 ten-day old chicks were fed a similar mash diet free of Antibiotic Compound 53,607 or its salts. They were also infected after 24 hours and served as infected controls. Yet other groups of 3-5 ten-day old chicks were fed the mash diet free of Antibiotic Compound 53,607 and were not infected with coccidia. These served as normal controls. The results of treatment were evaluated after five days in the case of *E. acervulina*, and six days for all other challenges. Table II summarizes the results obtained.

TABLE II

| Species Infection | Dose (ppm) | Average degree[1] of Infection | Ratio[1] | Weight Gain (%) |
|---|---|---|---|---|
| *Eimeria tenella* | 200 | 1.3 | 0.41 | 37 |
| | 100 | 1.0(1.3) | 0.32(0.37) | 57(60) |
| | 50 | 2.7(0.3) | 0.86(0.09) | 22(97) |
| | 25 | 3.0(1.7) | 0.95(0.49) | 47(102) |
| *Eimeria acervulina* | 200 | 1.5 | 0.75 | 2 |
| | 100 | 1.2 | 0.60 | 22 |
| | 50 | 2.0 | 1.00 | 18 |
| | 25 | 2.0 | 1.00 | 7 |
| *Eimeria necatrix* | 200 | — | — | — |
| | 100 | 0.0 | 0.00 | 69 |
| | 50 | 0.2 | 0.11 | 99 |
| | 25 | 0.6 | 0.33 | 111 |
| *Eimeria maxima* | 200 | 1.5 | 0.94 | 10 |
| | 100 | 0.8 | 0.50 | 37 |
| | 50 | 1.0 | 0.63 | 70 |
| | 25 | 1.4 | 0.88 | 51 |
| *Eimeria brunetti* | 200 | — | — | — |
| | 100 | 0.4 | 0.22 | 47 |
| | 50 | 1.0 | 0.55 | 49 |
| | 25 | 2.6 | 1.44 | 47 |

[1]The criteria used to measure anticoccidial activity consisted of lesion scores of 0 to 4 for *E. tenella* after J. E. Lynch "A New Method for the Primary Evaluation of Anticoccidial Activity.", Am. J. Vet. Res. 22:324–326 (1961); and 0 to 3 for the other species based on modification of the scoring system devised by J. Johnson and W. H. Reid, "Anticoccidial drugs. Lesion Scoring Techniques in Battery and Floor Pen Experiments in Chicks.", Exp. Parasit. 28:30–36 (1970). A constant ratio was established by dividing the lesion score of each treated group by the lesion score of the infected control.

The value of animal feeds generally has been determined directly by feeding the animal. British Pat. Specification No. 1,197,826 details an in vitro rumen technique whereby the changes occurring in feeds brought about by microorganisms are measured more readily and with great accuracy in the evaluation of animal feeds. This technique involves the use of an apparatus in which the digestive processes of the animals are conducted and studied in vitro. The animal feeds, rumen inoculum and various growth promotants are introduced into and withdrawn from a laboratory unit under carefully controlled conditions and the changes taken place are studied critically and progressively during the consumption of the feed by the microorganisms. An increase in the propionic acid content in the rumen fluid indicates that a desirable response in overall ruminant performance has been brought about by the growth promotant in the feed composition. The change in propionic acid content is expressed as percent of the propionic acid content found in the control rumen fluid. Long term in vivo feeding studies are used to show a reliable correlation between propionic acid increase in the rumen fluid and improved animal performance.

Rumen fluid is collected from a fistulated cow which is fed on a commercial fattening ration plus hay. The rumen fluid is immediately filtered through cheese cloth, and 10 ml added to a 50 ml conical flask containing 400 mg. of standard substrate (68% corn starch+17% cellulose+15% extracted soybean meal), ml. of a pH 6.8 buffer and the test compound. The flasks are gassed with oxygen free nitrogen for about two minutes, and incubated in a shaking water bath at 39° C. for about 16 hours. All tests are conducted in triplicate.

After incubation, 5 ml. of the sample is mixed with 1 ml. of 25% metaphosphoric acid. After 10 minutes 0.25 ml. of formic acid is added and the mixture centrifuged at 1,500 r.p.m. for 10 minutes. Samples are then analyzed by gas-liquid chromatography by the method of D. W. Kellog, *J. Dairy Science*, 52, 1690 (1969). Peak heights for acetic, propionic and butyric acids are determined for samples from untreated and treated incubation flasks.

When tested by this *in vitro* procedure, Antibiotic Compound 53,607 at the level of 20 micrograms per milliliter gave rise to about 57% increase in the production of propionic acid over that product in the control solution without added Antibiotic Compound 53,607. By comparison the commercially available Monensin (another polycyclic ether antibiotic) at 10 $\mu$g./ml. produced about 20% increase of propionic acid over the control [*J. Amer. Chem. Soc.*, 89 5737 (1967)].

When compared with Salinomycin [*J. Antibiotics*, 27:814, (1974)], Antibiotic Compound 53,607 produced about 43% increase in propionic acid at the level of 20 $\mu$g./ml. and about 40% increase at 5 $\mu$g./ml. compared with the increase of about 52% for Salinomycin at 5 $\mu$g./ml.

Based on this data, it can be projected that Antibiotic Compound 53,607 will improve feed utilization by ruminants such as cattle and sheep and by monogastric animals such as pigs and rabbits. Antibiotic Compound 53,607 may be incorporated in feed compositions as the free acid, sodium salt, potassium salt or mixtures thereof. Crude forms of Antibiotic Compound 53,607 or dried fermentation broth containing the antibiotic may be incorporated in feed compositions at the desired potency concentrations.

The following examples more fully illustrate the operation of this invention but it should be understood that the invention is not limited by the examples.

EXAMPLE I

Inoculum

A sterile aqueous medium having the following composition was prepared:

| Ingredient | Grams/liter |
|---|---|
| Cerelose | 10 |
| Starch | 20 |
| Yeast extract | 5 |
| NZ Amine YTT* | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant of *Streptomyces halstedii* ATCC 31812 were transferred to a series of 300 ml. flasks each containing 40 ml. of this sterile medium and shaken on a rotary shaker at 28°–36° C. for 3–4 days.

Fermentation

An aliquot of the grown culture, sufficient to provide a 2% v/v inoculum, was transferred to four liter fermentors each containing two liters of the following sterile medium:

| Ingredient | Grams/liter |
| --- | --- |
| Cerelose | 10 |
| NZ Amine A* | 5 |
| Starch | 20 |

*Registered trademark for enzymatic digest of casein, Humko Sheffield Chemical Co., Inc.

| Ingredient | Grams/liter |
| --- | --- |
| Yeast extract | 5.0 |
| Calcium carbonate | 1.0 |
| Cobalt chloride | 0.002 |
| Water to make 1000 ml. | |

Fermentation was carried out at 30° C. with stirring at 1700 revolutions per minute (RPM) and aeration at one volume air per volume of broth per minute until substantial activity was observed (based on antibiotic disc assay versus *B. subtilis* ATCC 6633*), usually 3–5 days. The whole broth was filtered at neutral pH employing a filter aid (Super Cel or Celite), the filtrate extracted with either methylisobutyl ketone or n-butanol. The organic phase was separated from the aqueous phase by aspiration and filtered to remove suspended material. The filter cake was slurried with methanol, filtered, the methanol evaporated and the residue extracted with the same solvent used for extration of the filtered broth. The extracts were combined and evaporated *in vacuo* to afford a viscous oil. The oil was suspended in heptane, stirred with silica gel and filtered. The filter cake was washed repeatedly with heptane and the product eluted stepwise with chloroform alone, mixtures of chloroform and ethyl acetate and finally with ethyl acetate alone. After thin-layer chromatography (TLC) and bioassay of the fractions, the active fractions were combined, evaporated *in vacuo* and the residue rechromatographed to obtain Antibiotic Compound 53,607 as a solid. Infrared spectrum (KBr disc) microns: 2.95, 3.42, 6.00, 6.37, 6.85, 7.14, 7.30, 7.65, 7.90, 8.10, 9.05, 9.15, 9.67, 10.00, 10.18. 10.53, 11.15, 11.40, 11.75, 13.25. It was found to be soluble in chloroform, ethyl acetate, methanol and methylisobutyl ketone; insoluble in water.

*The bioactivity of the broth, and subsequent recovery streams were followed by using a sensitive strain of *Baccilus subtilis* ATCC 6633 or *Staphylococcus aureus* ATCC 6538. The components in the broth and recovery streams were visualized by using silica gel plates in the following system: ethyl acetate/methanol 9:1, or chloroform/methanol 9:1 and the plate sprayed with vanillin (3 g. vanillin in 97.0 ml. ethanol and 3.0 ml. conc. sulfuric acid) then heated at 80° C. Compound 53,607 appears as a pinkish spot. Alternately, the plate was overlayed with agar, seeded with either *S. aureus* or *B. subtilis*, to which 1.0 ml. of a 1% tetrazolium solution was added, and incubated at 37° C. for 16 hours to visualize the antibiotic. (Clear areas against a pink background).

EXAMPLE 2

Inoculum was prepared as described in the previous Example, except that 700 ml. of medium per flask was employed, the shake flask inoculum fermented for 3–4 days at 28° C., composited in two side-arm bottles.

A 1700 gallon fermentor, containing 1200 gallons of the sterile medium below, was inoculated with six liters (0.1%) of the above inoculum:

| Fermentation Medium | |
| --- | --- |
| Ingredient | Grams/Liter |
| Cerelose | 1.0 |
| Casein | 5.0 |
| Starch | 5.0 |
| Corn steep liquor | 5.0 ml. |
| Calcium carbonate | 3.0 |
| Cobalt chloride | 0.002 |
| Water to 1 liter | |
| pH 6.9–7.0 | |

The fermentor was maintained at 28° C., with aeration and stirring at 1700 RPM. After 120 hours, the fermentor was harvested. The whole broth (1200 gallons) was extracted with 250 gallons methylisobutyl ketone, the layers were separated in an extractor (Podbielniak) and the organic phase concentrated *in vacuo* to obtain 8 gallons of oil. The oil was further concentrated *in vacuo* in a rotary evaporator. The residual syrup was suspended in heptane, stirred with silica gel and filtered, washing several times with heptane. The washed filter cake was worked up as described in Example 1 to obtain 300 g. of oil. The oil was dissolved in a small amount of chloroform, the solution poured onto a filter (Lapp) containing 3.5 kg. silica gel (Merck, grade 60) and the silica gel bed washed successively with 5 gallons each of chloroform, ethyl acetate and acetone. The fractions were examined by thin-layer chromatography. The product was found to be, almost exclusively, in the ethyl acetate fraction. The other fractions were discarded, the ethyl acetate fraction evaporated to dryness *in vacuo* to obtain 150 g. of concentrate. The concentrate was further purified by chromatography on an 8.0×1000 cm. column packed with silica gel (Merck, grade 60) by slurring with ethyl acetate. The column was eluted with ethyl acetate, taking 1 liter fractions at 60 ml./minute. The product-containing fractions were combined and evaporated *in vacuo* to yield 85 g. of product.

The product was passed through a column containing one kilogram of Sephadex LH-20, eluting with methanol at a flow rate of 25 ml./minute. Fractions of 300 ml. each were taken. Combining the product-containing fractions and evaporation of solvent afforded 30 g. of solid. This was dissolved in 500 ml. chloroform, the solution washed with an equal volume of 5% $NaH_2PO_4$ buffer which had been adjusted to pH 4.5 with 85% phosphoric acid. The organic phase was separated, washed with 500 ml. 5% $Na_2HPO_4$ buffer which had been adjusted to pH 9.0 with 1 N sodium hydroxide. The extract was then dried over anhydrous sodium sulfate and evaporated to dryness *in vacuo*. The residue was taken up in acetone and allowed to crystallize in the refrigerator. Crystals were collected by filtration and dried under high vacuum at room temperature to yield 14 g. of the sodium salt of Antibiotic Compound 53,607, M.P. 199°–204° C.

Optical rotation:
  $[alpha]_D +44°$ (c=1, chloroform)
  $[alpha]_D +37°$ (c=1, methanol).

Ultraviolet spectrum:
  $lambda_{max}$ 233 nm (methanol)

$E_{1\ cm.}^{1\%} = 212.$

Infrared spectrum (KBr disc) microns: 2.95, 3.42, 6.00, 6.37, 6.85, 7.14, 7.30, 7.65, 7.90, 8.10, 9.05, 9.15, 9.67, 10.00, 10.18, 10.53, 11.15, 11.40, 11.75, 13.25.

The infrared spectrum is shown in FIG. 1.

Elemental analyses: C, 57.54; H, 7.74; N, 0.0.

Employing $KH_2PO_4$ (pH 4.5) and $K_2HPO_4$ buffer adjusted to 9.0 with 1 N potassium hydroxide in the above procedure the potassium salt of Antibiotic Compound 53,607 is obtained in like manner.

Similarly, the ammonium salt is obtained by using $(NH_4)H_2PO_4$ and $(NH_4)_2HPO_4$ in the above procedure.

EXAMPLE 3

A portion of the above sodium salt of Antibiotic Compound 53,607 was dissolved in ethyl acetate, water added and the aqueous phase adjusted to pH 4.5 with 85% phosphoric acid. The organic layer was separated, dried ($Na_2SO_4$) and evaporated *in vacuo* to obtain the free acid of Compound 53,607, M.P. 84°–94° C. Elemental analysis was obtained on a sample dried overnight under high vacuum at room temperature:

C, 64.69; H, 8.91; N, 0.0.

The acid was found to be insoluble in water; soluble in chloroform, ethyl acetate, methanol and methylisobutyl ketone.

$[\alpha]_D +74.5°$ (c=1, chloroform)

$[\alpha]_D +49.7°$ (c=1, methanol).

Ultraviolet spectrum: $\lambda_{max}$ 233 nm (methanol)

$E_{1\ cm.}^{1\%} = 198$.

Infrared spectrum (KBr disc) microns: 2.95, 3.45, 6.00, 6.85, 7.28, 8.13, 9.05, 9.67, 10.20, 10.55, 11.15, 11.48.

The spectrum is shown in FIG. 2.

The barium salt is prepared by shaking 2.0 g. of free acid dissolved in 80 ml. ethyl acetate with an equal volume of water containing 2.4 g. barium hydroxide octahydrate. The layers are separated, the organic phase washed with a fresh solution of $Ba(OH_2.8H_2O)$, dried ($Na_2SO_4$) and evaporated *in vacuo* to give the desired salt of Antibiotic Compound 53,607.

The calcium salt is prepared by the above procedure, but employing calcium hydroxide in place of barium hydroxide octahydrate.

EXAMPLE 4

The procedure of Example 1 is carried out but employing 4% v/v inoculum in four liter fermentors, each containing two liters of the following sterile medium:

| Ingredient | Grams/liter |
|---|---|
| Cerelose | 10 |
| Corn starch | 10 |
| Soybean flour | 10 |
| Calcium carbonate | 1 |
| Corn fermentable solids | 5 |
| Sodium chloride | 5 |
| pH 7.0 | |

Fermentation was carried out for two days at 36° C. with stirring at 1700 RPM and air sparging at a rate of 2 volumes/ volume of broth per minute. The whole broth was extracted with chloroform and worked up as described in Example 1 to provide Antiobiotic Compound 53,607 as a mixture of its sodium, potassium and calcium salts.

When the above procedure is repeated but employing a fermentation medium containing glycerol in place of cerelose, fish meal or cottonseed meal in place of corn fermentable solids and carrying out the fermentation at pH 8.0, 28° C., for 6 days, the results are substantially unchanged.

What is claimed is:

1. The antibiotic of the formula

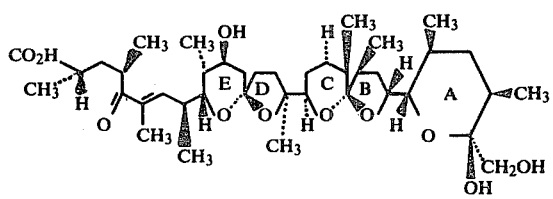

or the pharmaceutically acceptable salts thereof.

2. The antibiotic according to claim 1 in the form of a sodium salt.

3. The antibiotic according to claim 1 in the form of a potassium salt.

* * * * *

UNITED STATES PATENT AND TRADEMARK OFFICE
CERTIFICATE OF CORRECTION

PATENT NO. : 4,431,801
DATED : FEBRUARY 14, 1984
INVENTOR(S) : CELMER ET AL

It is certified that error appears in the above-identified patent and that said Letters Patent is hereby corrected as shown below:

Column 2, line 47, change " "Coaster fever" " to read
-- "Coastal fever" --.

In the Abstract, cover page, change the formula to read:

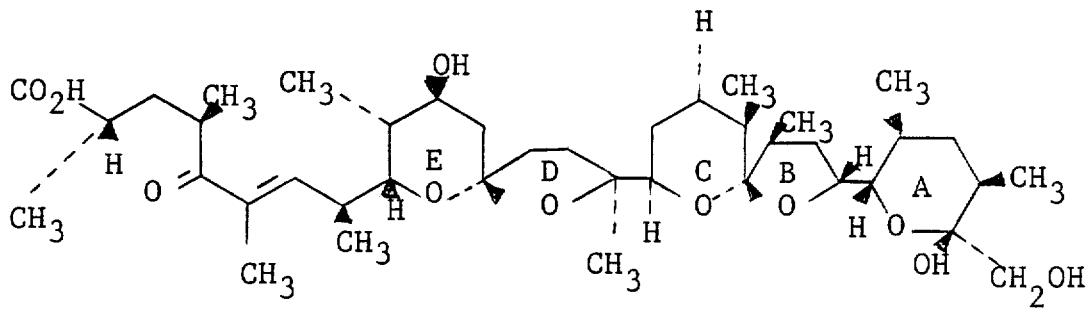

UNITED STATES PATENT AND TRADEMARK OFFICE
CERTIFICATE OF CORRECTION

PATENT NO. : 4,431,801
DATED : FEBRUARY 14, 1984
INVENTOR(S) : CELMER ET AL

It is certified that error appears in the above-identified patent and that said Letters Patent is hereby corrected as shown below:

Column 11, lines 10 to 25, rewrite the Table as follows:

--

| Ingredient | Grams/liter |
|---|---|
| Cerelose | 10 |
| NZ Amine A* | 5 |
| Starch | 20 |
| Yeast extract | 5.0 |
| Calcium carbonate | 1.0 |
| Cobalt chloride | 0.002 |
| Water to make 1000 ml. | |

* Registered trademark for enzymatic digest of casein, Humko Sheffield Chemical Co., Inc.         --.

Signed and Sealed this

Fifth Day of September, 1989

Attest:

DONALD J. QUIGG

Attesting Officer

Commissioner of Patents and Trademarks